US009655864B2

(12) United States Patent
Freyman et al.

(10) Patent No.: US 9,655,864 B2
(45) Date of Patent: May 23, 2017

(54) FIBERS COMPRISING POORLY SOLUBLE DRUGS AND/OR PROTEINS

(71) Applicants: Toby Freyman, Lexington, MA (US); Quynh Pham, Metheun, MA (US); Robert F. Mulligan, Arlington, MA (US); Abby N. Picard, Jamaica Plain, MA (US); Xuri Yan, Brighton, MA (US)

(72) Inventors: Toby Freyman, Lexington, MA (US); Quynh Pham, Metheun, MA (US); Robert F. Mulligan, Arlington, MA (US); Abby N. Picard, Jamaica Plain, MA (US); Xuri Yan, Brighton, MA (US)

(73) Assignee: Arsenal Medical, Inc., Watertown, MA (US)

( * ) Notice: Subject to any disclaimer, the term of this patent is extended or adjusted under 35 U.S.C. 154(b) by 171 days.

(21) Appl. No.: 14/211,900

(22) Filed: Mar. 14, 2014

(65) Prior Publication Data
US 2014/0227340 A1 Aug. 14, 2014

Related U.S. Application Data

(63) Continuation-in-part of application No. 13/758,173, filed on Feb. 4, 2013.

(60) Provisional application No. 61/852,233, filed on Mar. 15, 2013.

(51) Int. Cl.
A61K 9/70 (2006.01)
A61K 38/18 (2006.01)
A61K 31/496 (2006.01)
A61K 47/34 (2017.01)
D01D 5/00 (2006.01)
D01D 5/34 (2006.01)
D06M 15/03 (2006.01)
D01F 1/10 (2006.01)

(52) U.S. Cl.
CPC ............. *A61K 9/70* (2013.01); *A61K 31/496* (2013.01); *A61K 38/1825* (2013.01); *A61K 47/34* (2013.01); *D01D 5/0069* (2013.01); *D01D 5/34* (2013.01); *D01F 1/10* (2013.01); *D06M 15/03* (2013.01)

(58) Field of Classification Search
USPC ............... 424/443; 264/465; 514/9.1, 254.05
See application file for complete search history.

(56) References Cited

U.S. PATENT DOCUMENTS

| 2003/0095998 | A1* | 5/2003 | Pourdeyhimi ........... A61K 9/70 424/443 |
| 2005/0276841 | A1 | 12/2005 | Davis et al. |
| 2007/0134305 | A1* | 6/2007 | Zilberman ........... A61K 9/0092 424/443 |
| 2007/0232169 | A1 | 10/2007 | Strickler et al. |
| 2009/0196905 | A1 | 8/2009 | Spada et al. |

FOREIGN PATENT DOCUMENTS

| WO | WO9853768 A1 | 12/1998 |
| WO | WO0132229 A1 | 5/2001 |

* cited by examiner

Primary Examiner — Lynda Salvatore

(57) ABSTRACT

The present invention relates generally to the field of electrospun fibers. In particular, the present invention relates to core-sheath fibers and related electrospinning methods. The fibers of the invention comprise poorly water soluble drugs and/or proteins.

11 Claims, 4 Drawing Sheets

A.

B.

FIBERS COMPRISING POORLY SOLUBLE DRUGS AND/OR PROTEINS

CROSS-REFERENCE TO RELATED APPLICATIONS

This application claims priority to U.S. Provisional Patent Application Ser. No. 61/852,233 filed Mar. 15, 2013, entitled "Methods of Protein Encapsulation Using High Throughput Electrospinning," and further claims priority to U.S. patent application Ser. No. 13/758,173 filed Feb. 4, 2013, entitled "Electrospinning Process for Manufacture of Multi-Layered Structures." The entire disclosure of each of the foregoing applications is hereby incorporated by reference for all purposes.

STATEMENT OF GOVERNMENT SUPPORT

This invention was made with Government support under 70NANB11H004 awarded by the National Institute of Standards and Technology (NIST). The Government has certain rights in the invention.

TECHNICAL FIELD

The present invention relates generally to the field of electrospun fibers. In particular, the present invention relates to methods of producing core-sheath fibers using an electrospinning system. This electrospinning system can provide core-sheath microfibers loaded with a variety of therapeutic agents, including therapeutic proteins and poorly soluble drugs. The present invention also relates to methods of producing core-sheath fibers using an electrospinning system in which different types of polymer are present in the sheath solution and core solutions.

BACKGROUND

Drug loaded core-sheath fibers have been proposed for a number of medical applications, including for the localized delivery of therapeutic agents within a patient's body. Core-sheath fibers have several advantages over other drug delivery means, including relatively constant drug release that can be sustained over hours, days or weeks with relatively low levels of burst release, as well as the ability to tailor drug release kinetics according to the methods described in Sharma. Core-sheath fibers also allow formulations of drugs, polymers, excipients and other materials that are difficult or not possible to formulate into a monofiber. Implanted electrospun core-sheath fibers also provide highly localized release of therapeutics with a relatively low likelihood of unwanted migration from the site of implantation.

Methods of manufacturing core-sheath fibers loaded with small molecules including drugs have been described, and are discussed in Palasis II and Pham. However, scalable industrial methods for loading core-sheath fibers with an important category of therapeutic agents—proteins and peptides—have not been described. This is due in part to the technical challenges associated with working with proteins (namely, maintaining their activity and stability during and after their incorporation into fibers) in a manner that is economically feasible for industrial-scale fiber production. What is need is a method for producing protein-loaded core-sheath fibers in which the protein remains physically and chemically stable and retains its activity both during storage and after delivery to a patient.

SUMMARY OF THE INVENTION

In one aspect, the present invention relates to high-throughput methods of forming protein-containing electrospun core-sheath fibers by electrospinning a sheath solution that includes a bioresorbable polymer with a core solution that includes a protein in aqueous solution. In one embodiment, the method produces fibers having a core that includes the protein surrounded by a bioresorbable polymer sheath. In one embodiment, the core solution includes an excipient such as a polysaccharide (e.g. glucose, sucrose, trehalose or dextran), a protein (e.g. albumin), or a synthetic water soluble polymer (e.g. polyethylene glycol, polyvinyl alcohol and polyvinylpyrrolidine). In one embodiment, the protein is a growth factor, including (but not limited to), fibroblast growth factor 18 (FGF-18).

In another aspect, the present invention relates to methods of forming protein-containing electrospun core-sheath fibers by electrospinning a sheath solution that includes a synthetic bioresorbable polymer with a core solution that includes at least a partial suspension of a protein in a non-denaturing carrier. In one embodiment, the method forms fibers having a core that includes the protein and a bioresorbable polymer sheath surrounding the core. In one embodiment, the composition of the sheath is different than the composition of the core.

In another aspect, the present invention relates to methods of treating a patient by administering an electrospun core-sheath fiber with a protein-containing core, surrounded by a sheath, into the patient. In one embodiment, the composition of the sheath is different than the composition of the core. In one embodiment, the method includes placing the core-sheath fiber into the joint of a patient. In another embodiment, the protein contained within the core is a growth factor including, but not limited to, FGF-18.

In yet another aspect, the present invention relates to electrospun fibers with a diameter less than about 20 microns, wherein the fibers include an inner radial portion containing a protein and an outer radial portion that includes a binding agent for the protein. In one embodiment, the binding agent is optionally associated with an outer surface of the outer radial portion.

In yet another aspect, the present invention relates to electrospun fibers with a diameter of less than about 20 microns, wherein the fibers comprise an inner radial portion that includes a protein and a hydrogel, and an outer radial portion that does not include the protein. The protein is optionally at least partially suspended within the hydrogel.

In yet another aspect, the present invention relates to electrospun fibers that comprise one or more therapeutic agents in an amorphous or metastable state. In certain embodiments, the therapeutic agent(s) are located in the core and the fibers comprise one or more polymers that improve the stability of the therapeutic agent(s), and may also comprise excipients that improve the dissolution of the agents when administered to a patient.

In yet another aspect, the present invention relates to a method of forming a fiber that includes providing an electrospun fiber with a diameter of up to 20 microns, wherein the fiber comprises an outer radial portion as well as inner radial portion which includes a hydrogel, providing a saturated aqueous protein solution, and immersing the fiber in the protein solution so that the inner radial portion absorbs the protein. In various embodiments, the protein solution is supersaturated, and the outer radial portion of the fiber does not include hydrogel.

In yet another aspect, the present invention also relates to methods of producing core-sheath fibers using a core-sheath slit-surface electrospinning system in which different types of polymer are present in the sheath solution and core solutions. In one embodiment the sheath solution contains pure polymer. In one embodiment the core solution contains a poorly soluble drug. In one embodiment, the core-sheath fibers produced by the core-sheath slit-surface electrospinning system enhance the solubility of a poorly soluble drug included in the core solution.

BRIEF DESCRIPTION OF THE DRAWINGS

The above and further advantages of the invention may be better understood by referring to the following description in conjunction with the accompanying drawings, in which.

DETAILED DESCRIPTION OF THE PREFERRED EMBODIMENTS

Figure 1:
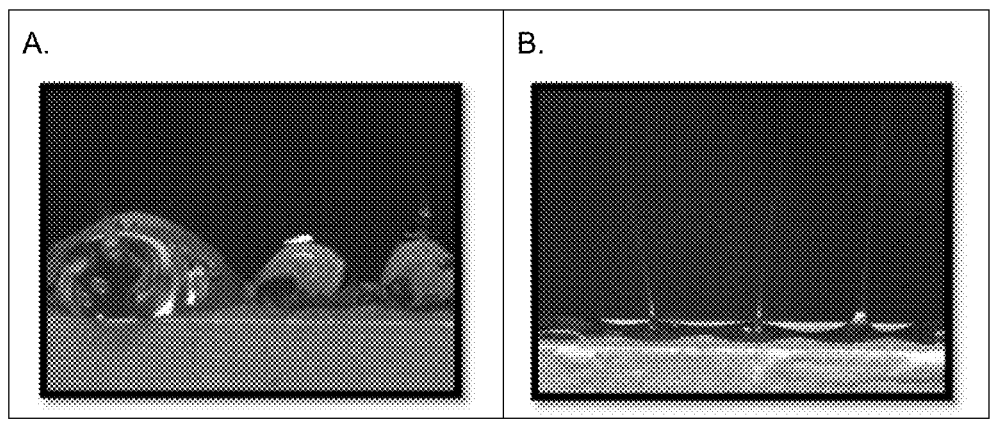
FIG. 1 compares electrospun jet formation from (A) a slit surface using HPMC in trifluoroethanol and (B) a slit surface using a core-sheath with HPMC in trifluoroethanol and PVP in trifluoroethanol.

The present invention relates to electrospun polymer fibers, methods of making such fibers, implants made from such fibers, and methods of treating patients using such fibers. The fibers of the present invention are capable of being loaded with a variety of drugs (e.g. drug-loaded fibers), excipients and/or binding agents. The methods of the present invention result in the manufacture of small fibers with surprisingly high protein and poorly-soluble drug loading rates, along with protein and drug release profiles capable of being tailored to the specific requirements of numerous medical applications. While various aspects and embodiments of the present invention have been described above, it should be understood that they have been presented by way of illustration rather than limitation. The breadth and scope of the present invention is intended to cover all modifications and variations that come within the scope of the following claims and their equivalents.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "protein" as used herein is intended to encompass peptides of all sizes and degrees of posttranslational modifications, including single amino acids of natural or synthetic origin, oligopeptides containing 2 or more residues, proteins, protein subunits and multi-subunit or multiprotein complexes, with or without posttranslational modifications of all types including without limitation phosphorylation, acetylation, N- or C-glycosylation, disulfide bonding, or the addition of functional or signaling moieties by covalent or non-covalent bonding, including the addition of lipid moieties, low molecular weight (e.g. methyl, acetyl, etc.) groups, ubiquitination SUMOylation, etc., the conversion of residues by carbamylation, deimination, deamination, decarboxylation, etc., the cleavage of covalent bonds including proteolysis, racemization, and the like.

The terms "drug" and "therapeutic agent" are used interchangeably to include small molecules, biologics, and other active ingredients used to produce a desired or expected biological effect, including the proteins used and described with reference to the present invention. The term "threshold concentration" and the like is used herein to describe a concentration in tissue, serum, plasma, etc. at which such a certain biological effect is observed, such as a therapeutic effect or a side effect. Thus, a "therapeutic threshold concentration" or similar term may be used to refer to an ED50, a dosing recommendation, or other effective concentration in the tissue of the patient. Similarly, the term "fiber" includes electrospun drug-loaded fibers such as homogeneous fibers and core-sheath fibers as described in Palasis II et al., as well as other drug-loaded fibers currently known that may be assembled into higher-order structures such as yarns, ropes, tubes and patches. In some embodiments, the drugs are said to be "poorly soluble," which according to the present invention shall mean a water solubility that is less than sparingly soluble, or solubility less than about 33 mg/ml, preferably less than about 10 mg/ml, and more preferably less than about 1 mg/ml.

As used herein, the term "consists essentially of" means excluding other materials that contribute to function, unless otherwise defined herein. Nonetheless, such other materials may be present, collectively or individually, in trace amounts.

As used herein, the terms "about," "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Core-Sheath Electrospinning

Electrospinning is a versatile technique for the production of small-diameter fibers of many natural and synthetic materials. This includes biopolymers (DNA, gelatin), liquid crystalline polymers (polyaramid), textile fiber polymers (nylon) and electrically conducting polymers (polyaniline) etc. (*J. of Macromolecular Science*, 36(2): 169 (1997); *J. of Biomedical Materials Research* 72(1): 156 (2005); *Nanotechnology* 7(3): 216 (1996); *Polymer* 43(3): 775 (2002); *Applied Physics Letters* 83(20): 4244 (2003)). Electrospinning utilizes a high electric field to extract a liquid jet of polymer solution from a liquid reservoir. Sufficient distance between the nozzle and substrate is required in order to fully evaporate the solvent. The highly charged liquid jet experiences bending and stretching effects due to charge repulsion and, in the process, becomes increasingly thinner. During this bending and whipping, the volatile solvent is thoroughly evaporated and the solidified fibers are collected on the conducting substrate. Advantages of electrospinning include the ability to control: a) the fiber diameter from micrometer to nanometer dimensions, b) the various fiber compositions and c) the spatial alignment of multiple fibers.

While this specification has focused on electrospinning and the formation of core-sheath fibers, the methods described above are also compatible with electrospinning of homogeneous (i.e. non-core-sheath) protein-loaded fibers that will be understood by those of skill in the art to be within the scope of the invention. Similarly, while one aspect of the present invention relates to protein-loaded electrospun core-sheath fibers and their methods of use and manufacture, those of skill in the art will appreciate that disclosures in this specification, particularly those relating to core-sheath fibers including hydrogels and methods of loading them, as well as core-sheath fibers including binding agents, are applicable to fibers loaded with non-protein drugs or bioactive agents.

Protein Loaded Fibers

In one aspect, the present invention relates to methods of producing core-sheath fibers that are loaded with therapeutic proteins using an electrospinning system in which a polymer solution is present in the sheath solution but not the core solution. In another aspect, the present invention relates to methods of producing core-sheath fibers that are loaded with therapeutic proteins using an electrospinning system in which the same polymer is present in both the sheath solution and core solution. In one aspect, the present invention relates to protein-loaded fibers, methods of making such fibers, implants made from such fibers, and methods of treating patients using such fibers. The present disclosure provides methods for manufacturing small fibers with high protein loading rates and drug release profiles that may be tailored to the specific requirements of numerous medical applications. In addition, the present disclosure provides a variety of implant configurations using the fibers of the present invention to optimize drug delivery characteristics and to facilitate appropriate deliverability of the implant to the patient and subsequent implant mobility.

In a preferred embodiment, the fibers of the present invention are manufactured using a high-throughput core-sheath electrospinning process (Pham et al.) in which separate core and sheath solutions are simultaneously co-localized to multiple sites of a Taylor cone formation. The methods of the invention are compatible with other electrospinning methods, including coaxial needles or, if homogenous fibers are desired, single needles or devices such as the Nanospider™ (Elmarco S.R.O., Liberec, Czech Republic). As used herein a "Taylor cone" refers to the approximately conical portion of a cone-jet produced during electrospinning, electrospraying and hydrodynamic spray processes from which a jet of charged particles emanates above a threshold voltage. When a small volume of electrically conductive liquid is exposed to an electric field, the shape of the liquid deforms from the shape caused by surface tension alone. As the voltage increases the effect of the electric field becomes more prominent, resulting in the formation of a cone with convex sides and a rounded tip as the force from the electric field approaches the surface tension of the liquid. When a threshold voltage is reached the slightly rounded tip of the cone inverts and emits a jet of liquid called a cone-jet. This represents the beginning of the electrospraying process in which ions are transferred to the gas phase. It is generally found that in order to achieve a stable cone-jet a slightly higher than threshold voltage must be used.

Any protein can be incorporated into fibers of the present invention, as is described in detail below. In preferred embodiments, the protein is a therapeutic protein such as an antibody or an active portion thereof (e.g. a Fab fragment), growth factor, hormone, receptor agonist or antagonist, RGD peptide, bacterial toxin or viral toxin, etc. In one example, the protein is a growth factor, including but not limited to, fibroblast growth factor 18 (FGF-18).

Protein-loaded fibers can be formed into implants comprising any number of fibers, including without limitation a single core-sheath fiber, a plurality of loose core-sheath fibers, or a plurality of grouped core-sheath fibers arranged into a structure such as a yarn, a rope, or a mesh. These structures are described in greater detail in Palasis II et al. In an exemplary embodiment, fibers loaded with FGF-18 are incorporated into an implant that is suitable for implantation into a joint, as for example described in Palasis I et al. In one embodiment the implant is placed in the intra-articular space of a joint in which cartilage has been damaged (as described in Palasis I et al.). FGF-18 loaded fibers and implants comprising such fibers advantageously permit localized delivery of FGF-18 to damaged cartilage while avoiding the deleterious effects that accompany more widespread or systemic delivery.

Core Solutions

If protein-loaded fibers are to be produced, the core solution preferably contains a therapeutic protein to be incorporated into the cores of the core-sheath fibers. In some embodiments, the core comprises an aqueous solution that includes a solution of therapeutic protein. Any suitable protein concentration may be used, including without limitation 100 mg/ml, 200 mg/ml, 300 mg/ml, 400 mg/ml, 500 mg/ml and 1 g/ml of protein. Suitable protein concentrations will vary depending on the protein to be encapsulated and the desired release profile desired. For instance, in some embodiments, the protein can be provided at a saturating or near-saturating concentration within the solution, so that the resulting fibers are maximally loaded with the protein.

More generally, the core solution can be tailored to the structure of the desired protein-loaded core and, by extension, the release kinetics thereof. Exemplary core solution formulations and their resultant core structures are set forth in Table 1.

TABLE 1

Core Solution Formulations and Resulting Protein-Loaded Core Structures

| Core solution | Protein form in core |
|---|---|
| Aqueous core only + protein | Grains |
| Aqueous + excipient + protein | Grains |
| Aqueous + water soluble polymer + protein | Distributed throughout polymer layer |
| Aqueous + water soluble polymer + excipient + protein | Distributed throughout polymer layer |

In some embodiments, the core solution includes a protein suspension in a non-solvent fluid carrier, such as cyclohexane or glycerol. Generally, any non-polar, non-denaturing carrier that does not denature the protein or otherwise promote unfolding of the protein during reconstitution is suitable for use in protein suspensions according to the invention. Low molecular weight polyols may also be used. The core solution can also contain one or more excipients to maintain and/or improve the solubility, stability and/or availability of the protein in the core solution and/or in the body after implantation of the resultant fibers.

As used herein, "excipients" are inert substances that serve as a vehicle for delivery of an active ingredient (e.g. therapeutic proteins, drugs etc.). In general, excipients can be added to reduce adsorption of proteins to surfaces during and after electrospinning, to prevent oxidation of proteins, to maintain a specific pH or tonicity, or to otherwise stabilize the protein. Excipients provide various therapeutic-enhancing purposes, such as facilitating solubility, systemic exposure, increased efficacy and/or drug absorption as well as other pharmacokinetic considerations including aiding in vitro stability such as preventing denaturation over the expected shelf life. (Today's Chemist at Work 10 (1): 30-36). The selection of appropriate excipients depends upon a variety of factors such as the route of administration, dosage form and the type of active ingredient. Excipients can also be added to ensure that the characteristics of the core solution (e.g., viscosity) are optimized for the electrospinning process. In one embodiment, the viscosity-tuning excipient is a polysaccharide, protein or bioresorbable polymer. Examples of polysaccharide excipients contemplated for use with the present invention include, without limitation, glucose, sucrose, trehalose and dextran. Examples of protein excipients contemplated for use with the present invention include (without limitation) albumin. Exemplary synthetic polymer excipients include (without limitation) polyethylene glycol (PEG), polyvinyl alcohol (PVA) and polyvinylpyrrolidine (PVP). A variety of excipients may be useful to promote protein stability during the electrospinning process and after the protein has been incorporated into polymer fibers. Examples of excipients are summarized by Jorgensen, et al., "Recent trends in stabilizing peptides and proteins in pharmaceutical formulation—considerations in the choice of excipients." *Expert Opin. Drug Deliv.* vol. 6, issue 11, pp. 1219-1230 (2009), and listed in Table 2.

TABLE 2

Exemplary Excipients

| Functional Effect | Excipient Category | Exemplary Excipients |
| --- | --- | --- |
| Anti-adsorption | Surfactants | Poloxamers, polysorbate 20, polysorbate 80 |
| | Polymers | Dextran, poly(ethylene glycol)-b-poly(L-histidine), polyethylene glycol |
| | Other proteins | Bovine serum albumin, human serum albumin, egg white albumin. |
| Oxidation protection | Antioxidants | Ascorbic acid, ectoine, glutathione, monothioglycerol, morin, poly(ethylenimine), propyl gallate, Vitamin E. |
| | Chelating Agents | Citric acid, ethylenediaminetetraacetic acid (EDTA), hexaphosphate, thioglycolic acid. |
| pH maintenance | Buffer salts | Phosphate, bicarbonate, sulphate, nitrate, acetate, chloride, pyruvate. |
| | Antacids | Magnesium hydroxide, (Mg(OH)$_2$), zinc carbonate (ZnCO$_3$) |

TABLE 2-continued

Exemplary Excipients

| Functional Effect | Excipient Category | Exemplary Excipients |
| --- | --- | --- |
| Stabilization | Amino acids | Alanine, arginine, aspartic acid, glycine, histidine, lysine, proline. |
| | Sugars | Glucose, sucrose, trehalose. |
| | Polyols | Glycerol, mannitol, sorbitol. |
| | Salts | Potassium phosphate, sodium sulphate. |
| | Chelating Agents | EDTA, hexaphosphate. |
| | Ligands | Phenol, zinc. |
| | Polymers | Cyclodextrin, dextran, PEG, poly(vinyl pyrrolidone) (PVP) |
| Tonicity maintenance | Salts | NaCl, etc. |
| | Non-polar solvents | Glycerol. |

Polysaccharide and protein excipients are particularly beneficially beneficial for the stabilization of proteins in core-sheath fibers. Without wishing to be bound to any theory, it is believed that these molecules promote the preferential hydration of protein surfaces, drawing water from the bulk of encapsulated proteins, and that such molecules also decrease homologous protein-protein interactions that may promote aggregation.

Sheath Solutions

Sheath solutions preferably include a bioresorbable polymer that is incorporated into the sheath of the resulting core-sheath fibers. Examples of bioabsorbable materials that are useful in core-sheath solutions of the present invention include: polyesters, such as poly(ε-caprolactone) (PCL), poly lactic-co-glycolic acid (PLGA), polyglycolic acid, poly (L-lactic acid), poly(DL-lactic acid); copolymers thereof such as poly(lactide-co-ε-caprolactone), poly(glycolide-co-ε-caprolactone), poly(lactide-co-glycolide), copolymers with polyethylene glycol (PEG); branched polyesters, such as poly(glycerol sebacate); polypropylene fumarate); poly (ether esters) such as polydioxanone; poly(ortho esters); polyanhydrides such as poly(sebacic anhydride); polycarbonates such as poly(trimethylcarbonate) and related copolymers; polyhydroxyalkanoates such as 3-hydroxybutyrate, 3-hydroxyvalerate and related copolymers that may or may not be biologically derived; polyphosphazenes; poly(amino acids) such as poly (L-lysine), poly (glutamic acid) and related copolymers. In other embodiments the sheath includes a biostable (i.e., non-bioabsorbable) polymer.

In one embodiment, the sheath solution includes an excipient such as collagen or heparin to enhance protein localization after its release from the core. Alternatively, excipients can be added to the sheath by post-processing steps such as chemical means or physical adsorption. In one embodiment, the sheath polymer is processed after electrospinning, including for example, cross-linking of the sheath polymers.

In other embodiments, electrospun core-sheath fibers of the invention include a core comprising hydrogel (e.g. PEG, polyacrylamide, x-linked PVA, x-linked PVP, etc.) and a sheath that lacks hydrogel. To load the core of such fibers with an active agent such as a protein, a fiber with a dehydrated core is at least partially immersed in an aqueous protein solution. As the solution diffuses or dialyzes across the sheath into the hydrogel core, the protein diffuses across the sheath as well. As used herein, "absorption" refers to the movement of the protein into the core by any passive mechanism, including without limitation diffusion or dialysis. After the protein has been absorbed into the hydrogel core; the fibers are optionally dried, evaporating the water but leaving behind the protein in particulate form.

Binding Agents

In some embodiments, the polymer fibers of the present invention can further include a binding agent that is capable of binding, adhering to or otherwise presenting a protein loaded onto the fiber. The presence of binding agents in the polymer fiber can improve protein activity and/or stability. Suitable binding agents include receptor molecules, cofactors, co-ligands, antibodies, nucleic acids, collagen, heparin or other small molecules that bind to the protein reversibly or irreversibly. In one embodiment, the binding agent binds the protein and preferably remains associated with an outer surface of the fiber, such as the outer surface of the sheath. In one embodiment, the binding agent is bound to the protein i) at the time the protein is loaded into the fiber, ii) after the protein is loaded into the fiber, but before the protein is eluted, or iii) after the protein is eluted. In one embodiment the binding agent is concentrated within the sheath. In another embodiment, the binding agent is concentrated in the core. In yet another embodiment, the binding agent is distributed throughout the core and the sheath. In still other embodiments, the binding agent is associated with an outer surface of the fiber, for example coating the surface, bound chemically by covalent or non-covalent means, or simply concentrated at or near the external surface. The binding agent can be added to either the core or sheath polymer solution prior to electrospinning, or it can be applied to the surface of the fiber after electrospinning, for example by powder coating. In some embodiments, the binding agent is covalently or non-covalently bound to a polymer in one or more of the sheath polymer solution and the core polymer solution.

Improved Solubility of Poorly Soluble Drugs

In one aspect, the present invention relates to methods of producing core-sheath fibers using an electrospinning system in which different types of polymers are present in the core and sheath solutions. This electrospinning system provides amorphous dispersions of core-sheath microfibers or nanofibers that enhance the solubility of poorly soluble drugs incorporated in the core and/or sheath solutions prior to electrospinning.

The core-sheath slit-surface electrospinning system of the present invention provides polymers with a small fiber diameter (micro- and nanometer), rapid solvent evaporation and full encapsulation of the core that cannot be achieved with other electrospinning methodologies. In one aspect, the core-sheath slit-surface electrospinning system provides formulations with improved solubility of poorly soluble drugs. In one embodiment, the improved solubility is due to the ability to include a variety of different polymers in the sheath and core solutions. In addition, the ability to incorporate pharmaceutical excipients directly into the fibers further expands the formulation space compared to conventional spinning techniques. Moreover, the slit-surface system provides an atypically long distance from the electrospinning nozzle to the collector (1 meter rather than one or tens of centimeters), thereby allowing for increased solvent evaporation prior to collecting as fibers.

The core-sheath electrospinning system includes a number of advantages as compared to existing electrospinning systems. For example, Yu et al. (Solid dispersions in the form of electrospun core-sheath nanofibers, 2011) provides a core-sheath electrospinning system consisting of 10% (w/v) PVP and 2% (w/v) acyclovir in a mixed solvent of DMAc:ethanol (4:6, v:v) as the core and 10% (w/v) PVP, 0.5% (w/v) SDS, and 0.2% (w/v) sucralose in a mixed solvent of water:ethanol (2:8, v:v) as the sheath. Unlike the system of Yu et al., the core-sheath slit-surface electrospinning systems of the present invention are capable of utilizing a variety of polymers in the core solution (e.g. HPMC) with a different polymer in the sheath solution (e.g., PVP). In addition, the core-sheath slit-surface electrospinning system is able to utilize pure polymers in the sheath solution. This represents a significant advantage over existing systems that must include additional components, such as SDS and sucralose, in the sheath solution to achieve satisfactory electrospinning. The solubility and stability of drugs incorporated within the core-sheath fibers of the present invention is further enhanced by the ability to include excipients (as discussed above) within nanofibers of the present invention.

One aspect of the fibers of the present invention is the high drug loading achieved. In certain embodiments, the drug loading rate is at least 80 wt % of the core of the fibers of the present invention. Moreover, unlike other fiber manufacturing processes, the systems and methods of the present invention may be used to form fibers that include one or more drugs in a substantially amorphous state notwithstanding that such drugs are otherwise stable in a crystalline state. As such, in certain embodiments, the fibers of the present invention comprise drugs in a metastable state, meaning that such drugs exist in a substantially amorphous state even though their most stable state is a crystalline form in the environmental conditions in which the fibers are used. As used herein, "substantially amorphous" means that the drug(s) are no more than 10% crystalline, and preferably no more than 5% crystalline. The ability to form fibers with drugs existing in metastable form is attributable to the high throughput electrospinning process of the present invention. That is, poorly (water) soluble, crystalline drugs are dissolved using organic solvents for use as core feed in the electrospinning process of the present invention. A separate polymer solution (free of drug in certain embodiments) is used as sheath feed. The rapid evaporation of the solvents during electrospinning prevents drug crystallization, thus yielding a core-sheath fiber structure with a core characterized by a high loading rate of drug that exists in substantially amorphous form. In other embodiments, the core optionally includes other drugs that are substantially amorphous or crystalline. In yet other embodiments, the sheath includes drugs that are in a crystalline state.

Core-sheath fibers of the present invention in which the core is characterized by a high loading rate of drug that exists in a metastable, substantially amorphous form have unique properties. For example, whereas the crystalline form of many drugs is poorly water soluble, the amorphous form may be significantly more water soluble. As such, the fibers of the present invention may be incorporated into capsules, tablets or other ingestible form for reliable drug drug delivery and bioavailability characterized by acceptable rates drug release and absorption. In contrast, it may be difficult for crystalline drug forms to be formulated such that they are adequately released and/or absorbed during passage through the gastrointestinal tract.

Poorly Soluble Drugs

One of the major challenges encountered in the development of innovative drug products is the poor solubility of most newly identified drug candidates. The use of conventional pharmaceutical dosage forms does not allow for sufficient drug dissolution in the human body and, therefore, leads to very low drug concentrations at the site of action (e.g., poor bioavailability). Consequently, even drug compound that offer ideal chemical structures to interact with their target sites often fail to perform satisfactorily in vivo.

In one aspect, the present invention improves the dissolution/solubility of poorly soluble drugs. This theoretically would improve its bioavailability when taken orally.

In one embodiment, the core-sheath slit-surface electrospinning system of the present invention is used to encapsulate the poorly soluble drug itraconazole (ITZ). Electrospinning of ITZ and other poorly soluble drugs significantly enhances their solubility, thereby increasing their bioavailability when administered to a patient. In one embodiment these electrospun fibers can be post-processed (e.g., cryomilled, hammer milled, molded, compressed, etc.) into solid oral dosage forms such as gelatin capsules, tablets and the like.

Polymer Selection

The development of core-sheath electrospinning materials that improve the solubility of poorly soluble drugs required identifying sheath polymer solutions, and specific wt % concentrations thereof, that exhibit good electrospinnability (i.e. form stable, non-solidifying Taylor cones). Without wising to be bound by any theory, the sheath solution is the primary factor in determining electrospinnability. Sheath solutions that exhibit favorable electrospinnability facilitate electrospinning of a range of materials/formulations in the core. In one embodiment, polymer selection is constrained to polymers that help pharmaceutical agents solubilize and release at the appropriate location within the body (e.g., the digestive system, circulatory system, respiratory system, nervous system, lymphatic system etc.). Such polymers include, but are not necessarily limited to, polyvinlypyrolidone (PVP), poly(vinylpyrrolidone-co-vinyl acetate), hydroxypropylmethyl cellulose (HPMC), HPMC acetate succinate, HPMC phthalate, cellulose acetate phthalate, ethyl cellulose, Eudragits, carbohydrates, and polyesters.

The core-sheath slit-surface electrospinning system of the present invention was used to identify sheath formulations with electrospinning properties capable of generating core-sheath fiber formulations that cannot be achieved using conventional electrospinning systems. As discussed previously, systems such as that of Yu et al. utilize the same polymer, and at the same concentration, (e.g. 10% w/v PVP) in both the core and sheath solutions. Moreover, to achieve favorable electrospinnability the sheath solutions of monofiber electrospinning systems must be mixed with SDS and sucralose. This is unlike the present core-sheath slit-surface electrospinning system which in which a variety of polymers in the core solution (e.g. HPMC, Soluplus®, and Eudragit®) can be electrospun with a different polymer (e.g., PVP) in the sheath solution. Moreover, optimizing the polymer concentration of the sheath solution allows good electrospinning to be achieved using sheath solutions comprising pure polymers (e.g. eliminating the need to add SDS and sucralose).

Figure 2:
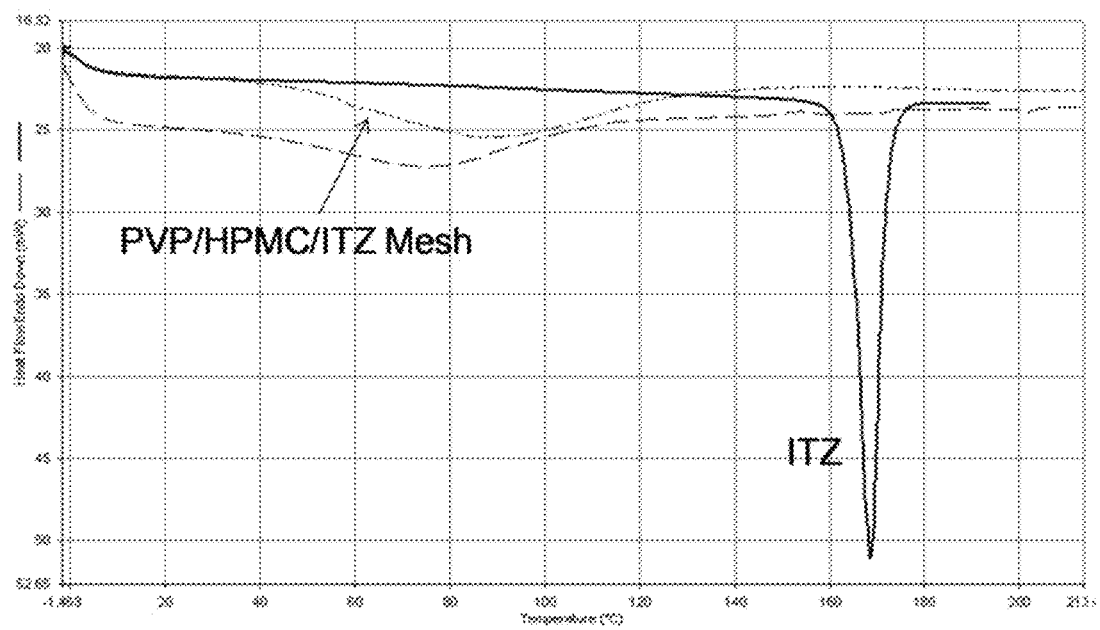
FIG. 2 depicts a scanning calorimetry thermogram illustrating the lack of a melting peak associated with crystalline ITZ in electrospun fibers of PVP/HPMC/ITZ.
Figure 3:
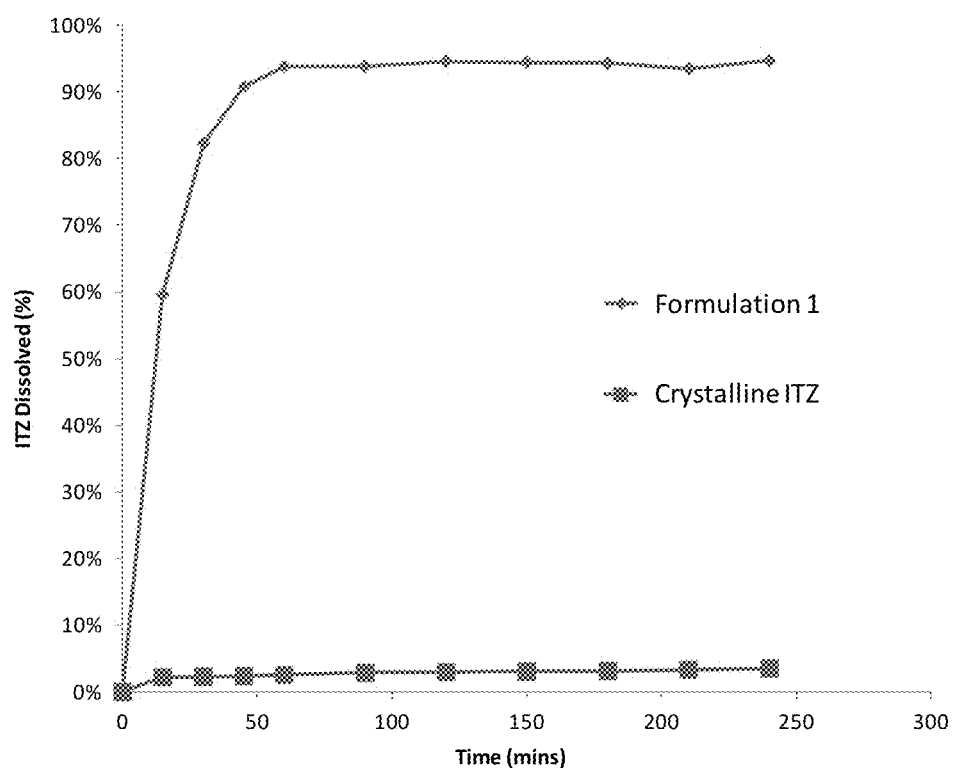
FIG. 3 shows the dissolution profile of core-sheath HPMC:ITZ-PVP fiber mesh.

Specifically, a sheath solution of polyvinylpyrrolidone (PVP) solution in trifluoroethanol (TFE) was identified as a polymer material that exhibits good electrospinning properties. The PVP sheath solution was co-electrospun with a core solution of hydroxypropylmethyl cellulose (HPMC) in trifluoroethanol containing using the slit-surface electrospinning nozzle. When electrospun as a core-only or monofiber the HPMC solution did not spin well, as evidenced by poor jetting that is likely due to solvent evaporation leading to solution solidification (FIG. 1A). However, good jetting and fiber collection occurred when the HPMC solution was electrospun as the core in a core-sheath system with PVP as the sheath (FIG. 1B). Collected fibers were dried in an oven to remove residual solvent. Differential scanning calorimetry revealed that the ITZ in the fibers did not have a melting peak associated with crystalline ITZ (FIG. 2). Dissolution testing of a mesh of HPMC:ITZ-PVP fibers was performed in simulated gastric fluid. FIG. 3 shows the dissolution profile of core-sheath fiber mesh of HPMC:ITZ-PVP demonstrating rapid and complete dissolution of the drug within an hour relative for crystalline ITZ. This data demonstrates that the electrospinning system and resulting material enhanced the solubility of ITZ.

Table 3 further illustrates the ability of the PVP sheath solution to facilitate electrospinning with a variety of core materials. This includes the incorporation of a number of pharmaceutical ingredients (excipients and surfactants) in both the core and sheath as well as substitution of the HPMC core with different polymers (e.g., HPMC; Soluplus®; Eudragit). The various HPMC core polymers further included various concentrations of ITZ relative to the percentage of each polymer. In one embodiment, ITZ is present in both the sheath solution and the core solution. Electrospinning of the material systems described in Table 3 occurred similarly as depicted in FIG. 1 and fibers were able to be collected in each case.

TABLE 3

Core materials electrospun with PVP sheath solution

| Formulation | Sheath solution | Core solution |
|---|---|---|
| 1 | PVP in TFE | HPMC in TFE containing 80% ITZ relative to polymer |
| 2 | PVP in TFE | HPMC in TFE containing 80% ITZ and 30% CaCMC relative to polymer |
| 3 | PVP in TFE | 17 wt % of 40:60 HPMC:ITZ in 60:40 DCM:EtOH |
| 4 | PVP in TFE | Soluplus® (polyvinyl caprolactam-polyvinyl acetate-polyethylene glycol graft co-polymer) in TFE containing 40% ITZ relative to polymer |
| 5 | PVP in TFE | Eudragit E100 in TFE containing 30% ITZ relative to polymer |
| 6 | PVP in TFE | 50:50 HPMC:Eudragit E100 in TFE containing 60% ITZ relative to polymer |
| 7 | PVP in TFE containing 30% Kolliphor 188 relative to polymer | HPMC in TFE containing 80% ITZ relative to polymer |
| 8 | PVP in TFE containing 60% CaCMC relative to polymer | HPMC in TFE containing 80% ITZ relative to polymer |
| 9 | PVP in TFE containing 50% ITZ relative to polymer | HPMC in TFE containing 80% ITZ relative to polymer |

Figure 4:
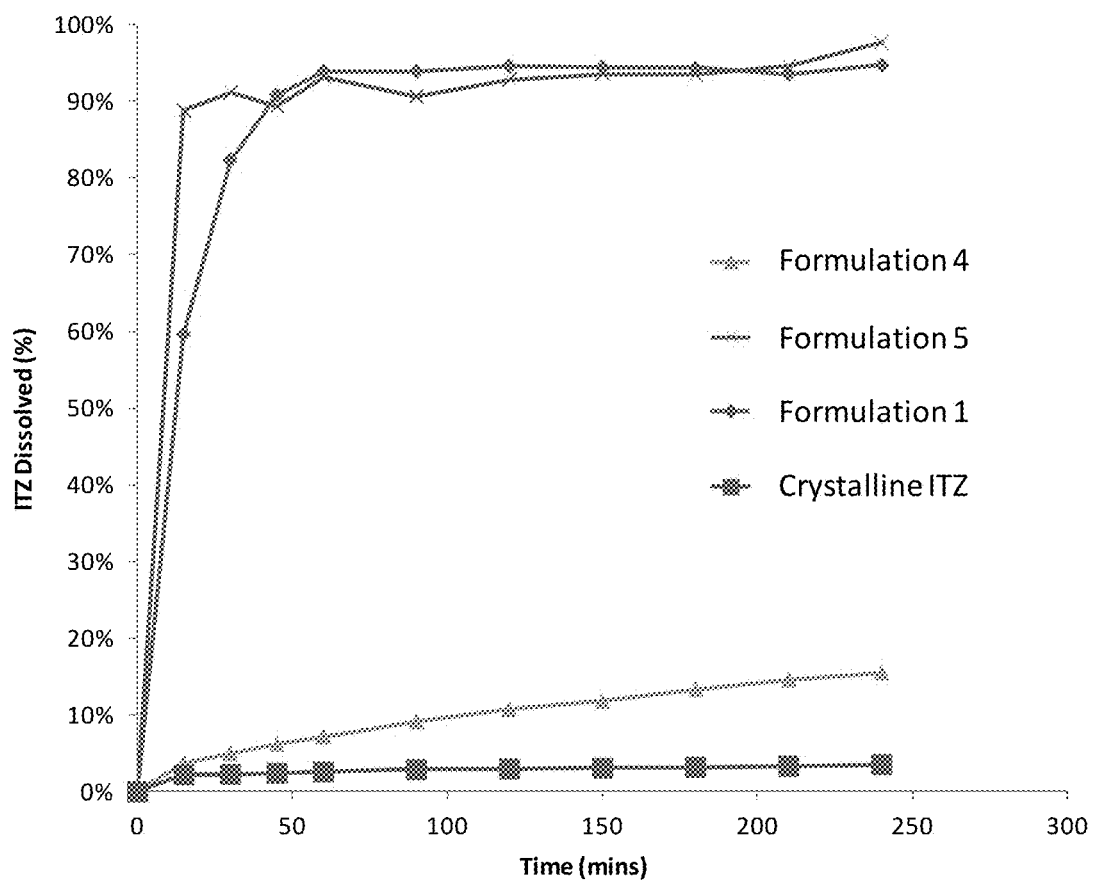
FIG. 4 shows the dissolution profiles of fiber mesh embodiments of the present invention.

FIG. 4 shows the impact of replacing HPMC with either Soluplus (Formulation 4) or Eudragit E100 (Formulation 5)

on ITZ release from meshes. It was observed that formulating ITZ with Soluplus resulted in improved dissolution relative to crystalline ITZ, but was significantly less than when formulated with HPMC. Conversely, formulating ITZ with Eudragit E100 had similar results as when formulating with HPMC. This data shows the value of core-sheath electrospinning with respect to achieving different dissolution metrics.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

We claim:

1. A structure, comprising:
   a core-sheath fiber comprising a core comprising hydroxypropylmethyl cellulose and a metastable first drug in a substantially amorphous state, said drug being poorly soluble in water; and
   a sheath comprising polyvinylpyrrolidine, said sheath surrounding said core.

2. The structure of claim 1, wherein the weight percent of said drug is at least 80% relative to said second polymer.

3. The structure of claim 1, wherein said structure is an ingestible capsule.

4. The structure of claim 1, wherein said structure is an ingestible tablet.

5. The structure of claim 2, wherein the crystallinity of said drug is 5% or less.

6. The structure of claim 1, wherein said core comprises a second drug in a crystalline state.

7. The structure of claim 1, wherein said sheath comprises a second drug in a crystalline state.

8. The structure of claim 1, wherein said fiber is characterized by a cross-sectional diameter of up to 20 microns.

9. An ingestible structure, comprising:
   a core-sheath fiber comprising a core comprising hydroxypropylmethyl cellulose and a metastable first drug in a substantially amorphous state, said drug being poorly soluble in water; and
   a sheath comprising polyvinylpyrrolidine, said sheath surrounding said core;
   wherein the weight percent of said drug is at least 80% relative to said first polymer, the crystallinity of said drug is 5% or less, and a cross-sectional diameter of said fiber is up to 20 microns.

10. The structure of claim 9, wherein said core comprises a second drug in a crystalline state.

11. The structure of claim 9, wherein said sheath comprises a second drug in a crystalline state.

* * * * *